United States Patent [19]

Esper et al.

[11] 4,228,128
[45] Oct. 14, 1980

[54] EXHAUST GAS SENSOR HAVING POROUS, METAL-IMPREGNATED CERAMIC ELEMENT

[75] Inventors: Michael J. Esper, Redford Township, Wayne County; Wells L. Green; Stanley R. Merchant, both of Garden City, all of Mich.

[73] Assignee: Ford Motor Company, Dearborn, Mich.

[21] Appl. No.: 21,374

[22] Filed: Mar. 19, 1979

Related U.S. Application Data

[63] Continuation-in-part of Ser. No. 839,701, Oct. 5, 1977, abandoned.

[51] Int. Cl.$^3$ ............................................. G01N 27/12
[52] U.S. Cl. ................................. 422/98; 23/232 E; 252/477 R; 60/276; 324/71 SN; 338/22 SD
[58] Field of Search .......................... 252/472, 477 R; 23/232 E; 422/119, 94–98; 60/276; 204/195 S; 338/22 SD; 324/71 SN

[56] References Cited

U.S. PATENT DOCUMENTS

| | | | |
|---|---|---|---|
| 2,782,103 | 2/1957 | Prentiss | 422/94 |
| 3,200,011 | 8/1965 | Baker | 473/27 R |
| 3,479,257 | 11/1969 | Shaver | 422/95 X |
| 3,564,474 | 2/1971 | Firth et al. | 422/95 X |
| 3,645,875 | 2/1972 | Record et al. | 204/195 S |
| 3,883,307 | 5/1975 | Kim | 252/477 R |
| 3,992,331 | 11/1976 | Petrow et al. | 252/472 |
| 4,058,485 | 11/1977 | Cheung | 252/477 R |
| 4,066,413 | 1/1978 | Segawa et al. | 422/98 |

Primary Examiner—Michael S. Marcus
Attorney, Agent, or Firm—Robert W. Brown; Clifford L. Sadler

[57] ABSTRACT

An improved sensor having a ceramic element that undergoes a change in an electrical characteristic in response to a change in the partial pressure of oxygen in a mixture of gases to which the ceramic element is exposed. Sensors of this type are used to detect the air/fuel ratio of mixtures supplied to internal combustion engines. Prior art sensors are characterized by little change in their respective electrical characteristics at low operating temperatures. A charge transfer material, platinum or platinum/rhodium is applied to the ceramic element to facilitate or make possible the electron transfers required for sensor operation at low temperatures. Platinum/rhodium alloy is the currently preferred charge transfer material. This alloy, which preferably is 90% platinum and 10% rhodium, reduces the minimum temperature of operation for the sensor as taught herein, and it also substantially eliminates vaporization loss of the charge transfer material.

5 Claims, 9 Drawing Figures

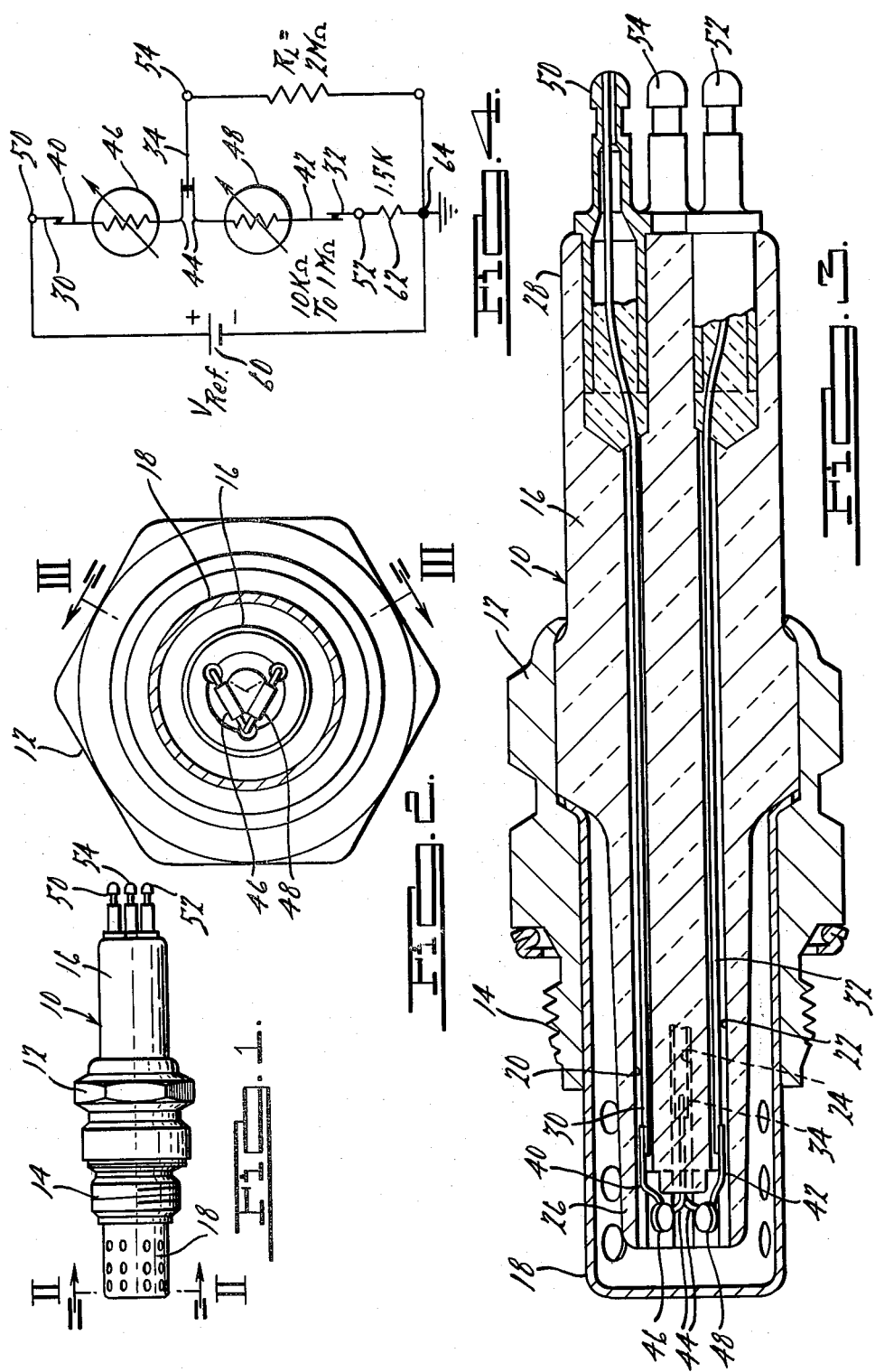

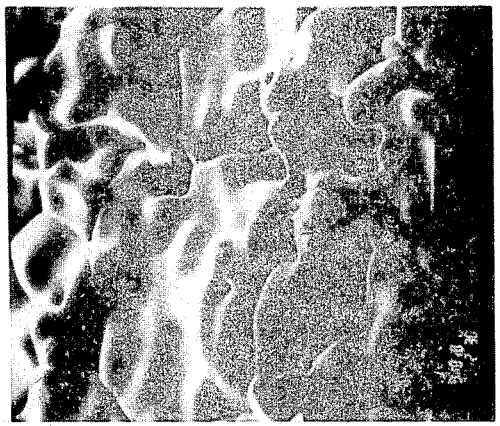
Fig. 6.
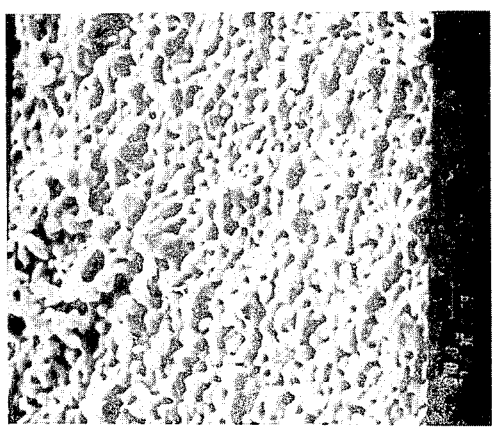
Fig. 5.

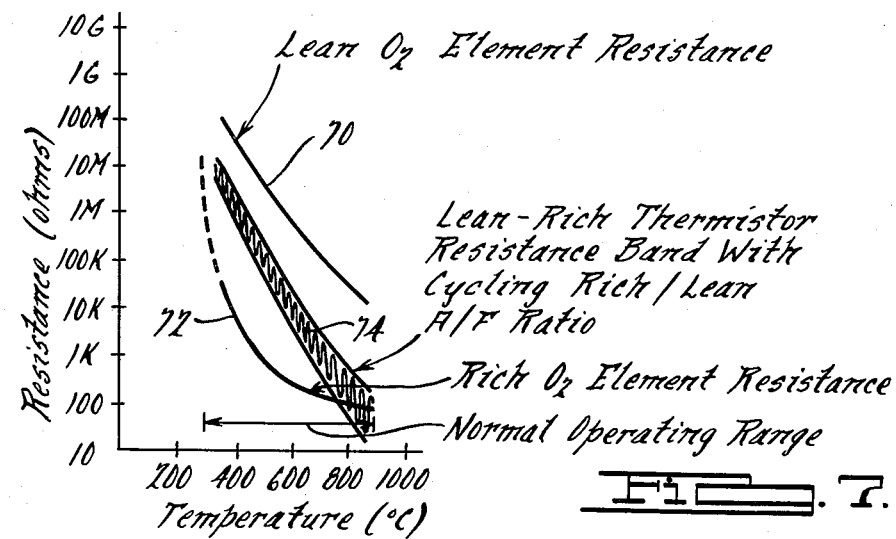
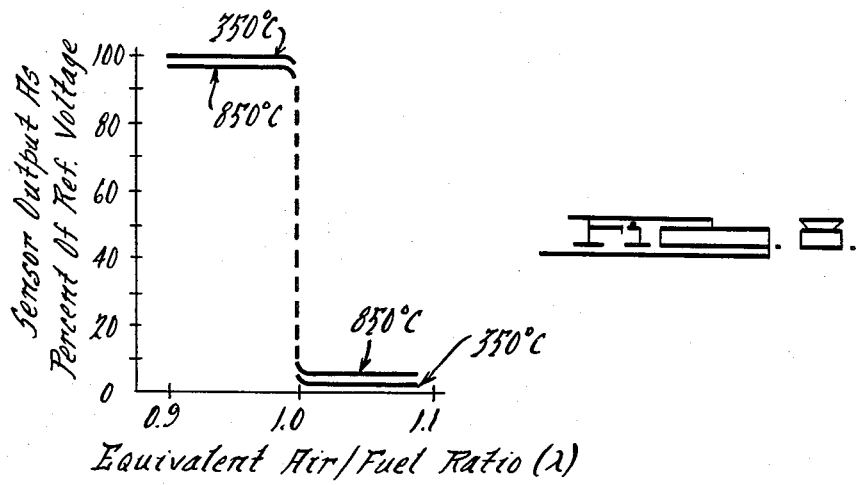
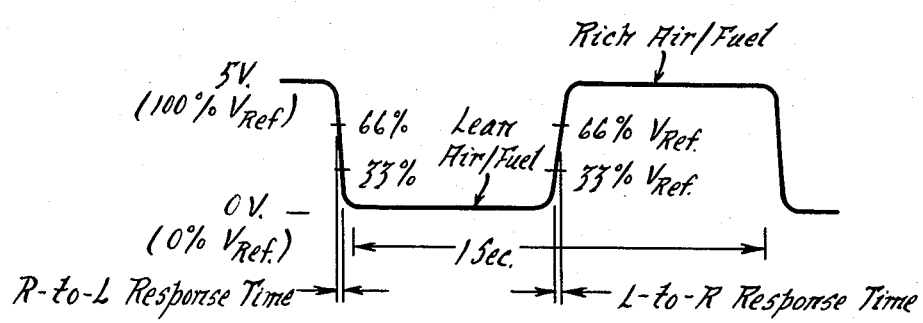

EXHAUST GAS SENSOR HAVING POROUS, METAL-IMPREGNATED CERAMIC ELEMENT

CROSS-REFERENCE TO RELATED APPLICATIONS

This is a continuation-in-part of patent application Ser. No. 839,701 filed Oct. 5, 1977, now abandoned in the names of of present inventors and entitled "Catalytic Material Impregnated, Porous, Variably Resistive Exhaust Gas Sensor and Method of Impregnation." This application also is related to commonly-assigned patent application Ser. No. 5,425 filed Jan. 22, 1979 and entitled "Improved Ceramic Element Sensor", which describes and claims an improvement in the subject matter hereof.

BACKGROUND OF THE INVENTION

This invention relates to an improved sensor of the type having a ceramic element that undergoes a change in an electrical characteristic in response to a change in the partial pressure of oxygen in a mixture of gases to which the ceramic element is exposed. The ceramic element of the sensor may be either titania or zirconia under the current state of development, but other electrically responsive ceramics are known and may be used in the future. The preferred titania ceramic element is porous to provide a large surface area for effecting the transfer of oxygen from the titania to the gases to which the ceramic element is exposed and vice versa. According to the present invention, the porous titania ceramic element has dispersed within it a discontinuous coating of a precious metal charge transfer material. In application Ser. No. 839,701 mentioned above, this precious metal charge transfer material was referred to as a "catalyst", a somewhat misleading designation.

Sensors of the type having a zirconia ceramic element also utilize a porous platinum charge transfer material, but the zirconia ceramic is very dense and the platinum is applied to the zirconia surfaces by vapor deposition. The surface platinum to be exposed to engine exhaust gases is usually covered with a porous refractory material to aid in bonding and for the protection of the platinum.

Sensors of the type discussed above are particularly suited for use in detecting excursions, above and below stiochiometry, of the air/fuel ratio of the mixture of air and fuel supplied to an internal combustion engine. In accomplishing this detection, the sensor is positioned in the path of the exhaust gases emanating from the engine. As the mixture supplied to the engine changes from rich to lean, the exhaust gases change from a composition including very littly oxygen to a composition containing an excess of oxygen. As the exhaust gases change from lean to rich, the reverse changes in composition occur. The sensors have an electrical characteristic that undergoes a step-function change as a result of the mixture excursions across the stoichiometric air/fuel ratio.

The titania ceramic material undergoes a change in its resistance as a function of the oxygen concentration gradient between the titania and the exhaust gases. The zirconia ceramic element undergoes a change in the EMF produced across its platinum change transfer electrodes as a function of the oxygen concentration differential on opposite sides of the zirconia material. With the zirconia sensor, a reference gas, usually air, is applied to one side of the zirconia and the exhaust gas composition is allowed to contact the other side of the zirconia. The use of a reference gas is unnecessary in connection with titania sensors, and the entire titania ceramic element is immersed in the exhaust gases.

The present invention is particularly directed to a titania sensor. The response time of the prior art titania sensor, to excursions from stoichiometry of the air/fuel ratio of the combustion mixture being provided to the internal combustion engine, is long (slow response) at exhaust gas temperatures in the lower portion of the normal operating temperature range. The prior art titania sensor has a normal operating temperature range that extends from about 525° C. to about 900° C. This is a range substantially narrower than that of the 350° C. to about 850° C. range of a typical zirconia exhaust gas sensor, and sensor operability at lower temperatures is a necessity if separate sensor heating devices are to be avoided. Failure of the prior art titania sensor to operate at low temperatures is a very serious problem because it means that the feedback fuel control system associated with the sensor for controlling the mixture ratios supplied to an internal combustion engine cannot be operated unless and until the exhaust gases have heated the sensor sufficiently to maintain its temperature above that at which it is able to respond to air/fuel ratio variations. This may increase undesirable engine exhaust emissions and reduce fuel economy during engine warm-up conditions.

The aforementioned technique of heating the titania sensor to avoid the response-time lag requires that the sensor be maintained at a preselected, elevated operating temperature. While this approach has proved to be functional, the reliability of the device is decreased and its manufacturing cost and complexity are excessive.

PRIOR ART PATENTS

The use of precious metal materials on ceramic element exhaust gas sensors and catalytic devices is known in the prior art. This is evidenced by the following U.S. patents, all of which were cited during prosecution of patent application Ser. No. 839,701 previously mentioned: U.S. Pat. Nos. 3,992,331 to Petrow et al; 4,059,485 to Cheung; 3,200,011 to Baker; 3,645,875 to Record et al; 3,883,307 to Kim; 4,066,413 to Segawa et al; 3,782,103 to Prentiss; 3,479,357 to Shaver; and 3,564,474 to Firth et al. Of these patents, Segawa et al patent 4,066,413 appears to be the most relevant to the subject matter hereof.

The Segawa et al patent describes a titania (titanium dioxide-$TiO_2$) ceramic element exhaust gas sensor responsive to the partial pressure of oxygen in exhaust gases from an internal combustion engine. The titania, or other metal oxide semiconductor material, in the sensor has applied to it a platinum catalyst which apparently is intended to promote a reaction between hydrocarbons and carbon monoxide in the exhaust gases with oxygen also contained therein when the exhaust gases are the products of combustion of a lean air/fuel mixture. Several embodiments are described, but the conclusion appears inescapable that the position of the electrodes of the sensor, relative to the surface of the detecting element which is to be exposed to the exhaust gases, is extremely critical. For example, in FIG. 26 of the Segawa et al patent, it may be seen that the response time of the sensor varies radically as a function of electrode depth.

SUMMARY OF THE INVENTION

The invention provides a metal oxide, ceramic exhaust gas sensor element that has a substantially improved (reduced) response time to variations in exhaust gas composition that result from corresponding variations above and below stoichiometry of an air/fuel mixture whose combustion produces the exhaust gases.

In the preferred form, the metal oxide ceramic is sintered titania with a porous physical structure. Suitable electrode wires are embedded in the titania material in spaced apart relationship. Variations in the partial pressure of oxygen in the exhaust gases to which the porous titania is adapted to be exposed cause corresponding variations in the electrical resistance between the electrodes embedded therein.

The response time of the metal oxide oxygen ceramic sensing element described above is improved by the deposition on its surfaces of a discontinuous or porous electrical-charge-transfer material. For the purpose of increasing the amount of surface area of the metal oxide ceramic material that is exposed to the exhaust gases, the physical structure of the ceramic is deliberately made porous. This enlarged surface area is desirable because it facilitates the reversible transfer of oxygen atoms or ions into the crystal structure of the metal oxide ceramic material. Oxygen entering or leaving the crystal structure alters the number of oxygen vacancies therein and, as a result, changes the resistivity of the material. A change in the partial pressure of oxygen in the gaseous medium to which the metal oxide is exposed causes the oxygen atoms or ions to enter or leave the metal oxide material.

The response time of the metal oxide material to variations in oxygen partial pressure is long at low metal oxide material temperatures probably because of the unavailability of electrons required to allow oxygen to enter and leave the metal oxide crystal structure. It is speculated that at higher metal oxide material temperatures, electrons become more available for use in oxygen transfer and that this substantially explains the improved response time of metal oxide resistive exhaust gas sensors at their higher operating temperatures.

The present invention provides improved low-temperature response of metal oxide resistive sensors by supplying a source of electrons. This source is in the form of a precious-metal charge transfer material deposited on the multitudinous surfaces of the porous metal oxide ceramic. Discontinuous or porous metal surfaces are formed on the metal oxide ceramic surfaces. Much of the metal oxide surface area is unoccupied by the metal surfaces so that oxygen can be transferred into and out of the metal oxide crystal structure, but the nearby metal surfaces provide a convenient source or "pool" of free electrons that assist in the transfer of charge between atoms and ions. For this reason, the metal surfaces on the metal oxide constitute a "charge transfer material".

The metal surfaces preferably are uniformly dispersed throughout the porous metal oxide material. This may be accomplished at least substantially by immersion of the metal oxide material in a solution of a metal compound or salt that, after drying, may be decomposed to produce the discontinuous metal surfaces within the porous metal oxide ceramic material.

The invention may be better understood by reference to the detailed description which follows and to the drawings:

BRIEF DESCRIPTION OF THE DRAWINGS

FIG. 1 is an elevational view of a titania exhaust gas oxygen sensor suitable for installation in the intake manifold of an external combustion engine;

FIG. 2 is a sectional end view, taken along the line II—II in FIG. 1, of the sensor of FIG. 1 and is shown in enlarged scale;

FIG. 3 is a sectional view, taken along the line III—III in FIG. 2, showing the internal structure of the sensor of FIGS. 1 and 2 also on an enlarged scale;

FIG. 4 is a circuit diagram illustrating the manner in which the titania oxygen sensing element and the thermistor shown in FIGS. 1 through 3 are electrically connected with circuitry designed to receive the sensor output voltage;

FIGS. 5 and 6 are photomicrographs of the titania oxygen sensor and the thermistor illustrated in FIGS. 1 through 4;

FIG. 7 is a graph of both the oxygen sensor element and thermistor element resistance as a function of temperature over the operating temperature range from about 300° C. to about 900° C.;

FIG. 8 is a graph of sensor output voltage as a percent of the input (reference) voltage versus equivalent air/fuel ratio;

FIG. 9 is a graph illustrating the voltage response of the titania sensor as a function of time with an air/fuel ratio that varies by about 0.1 ratios above and below stoichiometry;

DETAILED DESCRIPTION

With particular reference now to FIGS. 1 through 3, wherein like numerals refer to like parts in the several views, there is shown a complete titania exhaust gas sensor assembly generally designated by the numeral 10. The sensor 10 includes a steel housing or body 12, which may be substantially identical to a typical spark plug body, having a threaded portion 14 for engagement with a suitably threaded aperture provided within the exhaust system of an internal combustion engine (not shown). In most cases, the sensor 10 would be installed in an aperture at a location in the exhaust manifold near the flange that would connect to an exhaust pipe. A ceramic insulator 16 extends through the body 12 and has a tapered portion 26 projecting outwardly from the body 12 into the volume defined by the boundaries of a perforated shield 18. There are three longitudinal passages 20, 22 and 24 extending from the projecting end 26 of the ceramic insulator to its opposite end 28. Wires 30, 32 and 34 are located in the respectively corresponding passages 20, 22 and 24 and are of a heat resistant character, preferably being made from an alloy such as 80% nickel-20% chromium wire. These electrically conductive wires are welded to precious-metal wire leads 40, 42 and 44, which are embedded in disc-shaped ceramic elements 46 and 48.

Element 46 is a ceramic metal oxide and, preferably, titania $O_2$ sensor element responsive to the partial pressure of oxygen in the gaseous medium to which this element is exposed. Sensor element 46 is fabricated in accordance with the teachings of commonly assigned U.S. Pat. Nos. 3,886,785 issued June 3, 1975 and 3,932,246 issued Jan. 13, 1976, both in the names of Stadler et al. The teachings of the present invention must, however, also be considered in the fabrication of the oxygen sensing element 46. The present invention teaches the application to the porous metal oxide ceramic oxygen sensor of a metallic and discontinuous charge transfer material for reasons which are hereinafter made clear.

The element 48 is a thermistor. The thermistor may be made from titania ceramic material of greater density, near its theoretical density, than the density of the porous titania oxygen sensor 46. Alternatively, the thermistor 48 may be constructed in accordance with the teachings of copending and commonly assigned U.S. patent application Ser. No. 857,498 filed Dec. 5, 1977, now U.S. Pat. No. 4,162,631, in the names of Logothetis, Laud and Park and entitled "Rare Earth—Yttrium, transition metal oxide Thermistors". The thermistor 48 is intended to provide temperature compensation in accordance with the circuitry illustrated in FIG. 4 and is intended to be substantially nonresponsive to variations in the partial pressure of oxygen in the gaseous medium to which it is exposed.

The sensor of FIGS. 1 through 3 is intended to be used in conjunction with electronic circuitry for closed-loop feedback control of the amount of fuel supplied to an internal combustion engine. The sensor indicates whether the exhaust gases contain a substantial amount of HC and Co or whether instead there is a substantial amount of oxygen, thereby, indicating whether or not the air/fuel ratio of the mixture supplied to the engine was rich or lean with respect to the stoichiometric value of about 14.7 parts of air to each part of fuel by weight. This air/fuel ratio typically is expressed as a normalized air/fuel ratio lambda, wherein the actual ratio is divided by the stoichiometric value and the stoichiometric ratio therefore is represented as 1.0 in accordance with well known practice.

The exhaust gas sensor 10 has terminals 50, 52 and 54 designed for connection to external circuitry as specified above to enable it to be used in a feedback fuel control system. With particular reference now to FIG. 4, there is shown a circuit that schematically represents the manner in which the sensor 10 is utilized in association with such external circuitry. A DC source of regulated reference voltage 60 has its positive terminal connected to terminal 50 of the sensor oxygen responsive element 46. The lead wires 40, 42 and 44 from the sensor 46 and thermistor 48 are welded or otherwise joined, respectively, to lead wires 30, 32 and 34 to interconnect the two ceramic elements 46 and 48 as shown. The thermistor element 48 is connected through a response-shaping resistor 62 to ground potential at 64. The output voltage of the sensor 10 is taken between the sensor terminal 54 and ground potential. This signal is applied across the input impedance or load resistance $R_L$ (about two megohms) of the engine control electronic circuitry.

The input voltage to the circuit of FIG. 4 is obtained from the source referenc 60 and is applied across the voltage divider comprising the series-connected variable resistances of oxygen sensor 46 and thermistor 48 in series with the response-shaping resistor 62. The output voltage is taken across the load resistance $R_L$.

The resistance values of both the oxygen sensor 46 and the thermistor 48 vary as a function of temperature and in the same direction, that is, the resistance of these elements decreases with increasing temperature. As a result, the voltage dividing effect provides an output voltage across the load resistance $R_L$ that is independent of temperature. The oxygen sensor 46, however, has a resistance which varies not only with temperature but also with the partial pressure of oxygen in the gaseous medium to which the sensor is exposed. An increase in the resistance of the oxygen sensor 46 causes the output voltage across the load $R_L$ to decrease, and a reduction in the resistance of the oxygen sensor causes a corresponding increase in the output voltage across the resistance $R_L$. Otherwise stated, an increase in oxygen content in the gaseous medium surrounding the oxygen sensing device 46 causes its resistance to increase in a manner hereinafter described and thereby causes a reduction in the voltage across the load resistance $R_L$. A decrease in the oxygen content of the gaseous medium causes the resistance of the oxygen sensor 46 to decrease in a corresponding manner and this causes an increase in the voltage across the load resistance $R_L$.

FIG. 5 is a photomicrograph of the titania oxygen sensor 46 with a magnification of 700 times size. FIG. 6 is a photomicrograph of a titania thermistor 48 with a similar magnification of 700 times size. From the FIG. 5 titania sensor photomicrograph, it may be seen quite clearly that the oxygen sensor structure is very porous. Also, its grain size is very small as compared to the much larger grain size of the titania thermistor, which is much more dense and which lacks the porosity of the titania oxygen sensor.

Titanium dioxide (titania) is a material that occurs naturally in mixture with other minerals. The titania is obtained by precipitation from a solution of minerals that include titania. When thus obtained by precipitation, the titania has an anatase crystal structure. When the titania material in this crystal structure is formed into an exhaust gas oxygen sensor, it is first thermally treated in a manner that allows the crystal structure to change from anatase to rutile. An increase in the temperature of the rutile material above room temperature induces oxygen vacancies into the crystal structure. This results in ionization of the titanium atoms interstitially located in the crystal structure. The concentration of the interstitial titanium ions and oxygen vacancies increase as temperature rises, and these variations in concentration are of considerable significance in the use of titania as a sensor material.

FIG. 7 illustrates the manner in which the resistance of the oxygen sensing element 46 and the thermistor element 48 vary as a function of temperature. Curve 70 represents the resistance of the oxygen sensor when it is located in the exhaust gas emanating from an internal combustion engine supplied with a lean air/fuel mixture, that is, a mixture that has a quantity of oxygen greater than that required for stoichiometric combustion. The curve 72 represents the resistance of that sensor when located in the exhaust gases emanating from an engine supplied with a rich mixture. Curve 74 illustrates the resistance of the thermistor 48 as a function of temperature. The curve is of alternating character indicating the small variation of the thermistor resistance that occurs as the air/fuel ratio supplied to the engine oscillates back and forth about stoichiometry. From curve 74, it is quite evident that there is but very minor variation in the resistance of the thermistor 48 as a function of the oxygen content in the gaseous medium surrounding the sensor. This is much in contrast to the curves 70 and 72 representing, respectively, the lean and rich resistance values over the normal operating range of exhaust gas sensor 10. Of course, the actual resistance values for the oxygen sensor element 46 would vary back and forth between the curves 70 and 72 as the air/fuel ratio supplied to the engine was varied about stoichiometry. At the left side of the graph of FIG. 7, it may be seen that the curves 70 and 72 come together at low temperatures. This indicates that titania is not responsive to the surrounding oxygen concentration at low temperatures.

A very significant feature of the present invention is that the portion of the curves 70 and 72 at which the sensor becomes responsive to oxygen concentration occurs at a lower temperature than with the prior art device. This feature provides very substantial benefits.

The fact that rutile titania, as previously described, has deficiencies where atoms of oxygen are missing is responsible for much of the resistance variation indicated in FIG. 7.

If it is assumed that a titania sensor, such as sensor element 46, is located in an environment in which the oxygen concentration is constant and only the temperature varies, then the number of vacancies in the titania structure may change due to thermal energy. However, the titanium atom in those titanium oxide molecules having but one oxygen atom, have only two of their four valance electrons covalently bonded with oxygen. As the temperature of the titania increases, the thermal energy supplied to the molecules in the structure increases and the oxygen vacancies therein have greater mobility. As the oxygen deficiency and concentration of Ti interstitials increases, more electrons become available for the conduction process, and the resistivity of the material decreases. The conductivity of the titania increases or, otherwise stated, its resistance decreases as a function of temperature, as is indicated in FIG. 7 for both the thermistor and oxygen sensor element.

If it is now assumed that a sensor element 46 of titania is positioned in an environment of varying oxygen partial pressure and that it is at a temperature within the titania operating range, for example 600° C., then the number of vacancies in titania increases or decreases as a function of oxygen partial pressure.

If a titania oxygen sensor 46 is positioned in the exhaust stream of an internal combustione engine and if the air/fuel mixture supplied to such engine continually varies between lean and rich with respect to stoichiometry, the partial pressure of oxygen to which the sensor is exposed varies cyclically. When the mixture is lean, there is an excess of oxygen in the exhaust gas and few oxidizable carbon compounds. The titania element has a relatively high resistance, on the order of about 0.5 megohms. This is because oxygen from the exhaust gases will have been adsorbed on the surface of the titania element. The adsorbed oxygen atoms on the titania surface annihilate oxygen vacancies and interstitial titanium ions and migrate into the titania crystal structure. In an oxygen deficient oxide, both oxygen vacancies and interstitial ions may be involved in an equilibrium reaction with oxygen in the surrounding environment. In this equilibrium reaction, the partial pressure of oxygen in the environment determines whether the interstitial ions or the oxygen vacancies play the predominant role in the oxygen transfer process. In both cases, there is an acquisition of electrons followed by an annihilation of a vacancy and an interstitial ion. The electrons at low sensor operating temperatures are provided by the charge transfer material, which is an electrical conductor having a "pool" of available electrons. At higher temperatures, thermal energy is sufficient to provide electrons required at the titania surface for the process of vacancy annihilation. The lower the number of vacancies in the titania crystal structure, the higher is its electrical resistance. On the other hand, the more vacancies that are created in the crystal structure, the lower is the titania resistance.

When the exhaust gases change from lean-to-rich (L-R), a percentage of the oxygen atoms in the titania structure are removed to create additional vacancies. The oxygen leaves the titania crystal structure probably as a negatively charged ion. As a result, there is a positively charged vacancy left behind. At the titania surface, either the oxygen ion reacts with an oxidizable carbon compound in the exhaust gas or two oxygen atoms or ions unite to form an oxygen molecule.

When the exhaust gases change to a composition corresponding to a lean mixture, the concentration of oxidizable carbon compounds is drastically reduced and an excess of oxygen appears in the exhaust gas. The oxygen concentration gradient reverses, and oxygen atoms are adsorbed on the titania surface and fill vacancies therein as was previously mentioned.

FIG. 8 illustrates the manner in which the output voltage of the sensor 10, connected in the circuit of FIG. 4, varies as a function of air/fuel ratio where this ratio changes from rich (below 14.7) to lean (above 14.7). When the mixture is rich, the sensor element 46 has a low resistance and the sensor output voltage is almost 100 percent, the percentage figure being the ratio of the actual output voltage to the input reference voltage multiplied by 100 percent. It may be seen that, with the temperature compensation provided by the thermistor 48, there is very little variation in the sensor output voltage as a function of variation in temperature between 350° C. and 850° C. Under rich conditions, the removal of oxygen from the titania structure to create new vacancies provides additional electrons from the titanium atoms that may be used for the purpose of conduction. This explains the greatly increased conductivity of titania when exposed to exhaust gases produced by the combustion of rich mixtures. The opposite effect explains the very high resistance and low conductivity of the titania sensor element when exposed to exhaust gases produced by lean mixtures.

According to the teachings of the present invention and prior U.S. patent application Ser. No. 839,701 of which this application is a continuation, a metal is applied to the surface of the titania sensor element 46. The metal is referred to herein as a "charge transfer material" and is dispersed as much as possible on all of the interior and exterior surface areas of the porous titania element for the purpose of enhancing its response characteristics at low temperatures.

The use of the term "catalyst" to describe the metallic material dispersed throughout the titania element is believed to be a misnomer; little or no catalytic action is believed to take place. The metal with which the titania is impregnated functions as a charge transfer meterial to promote, particularly at the lower portion of the sensor operating range, the acquisition and removal of oxygen from the titania crystal structure as a result of air/fuel changes from rich-to-lean and lean-to-rich, respectively. The metal is very thin and may be located at or near the grain boundaries of the titania and is discontinuous to facilitate the acquisition and removal of oxygen from the titania.

When U.S. patent application Ser. No. 839,701 was filed, pure platinum was the preferred metal for use as what is now referred to as a charge transfer material.

Any metal, however, that can be retained in its elemental state as a source of free electrons is thought to be functionally satisfactory as a charge transfer material. Precious metals are preferred due to their resistance to chemical reaction. Specifically, an alloy of platinum and rhodium currently is thought to be the best charge transfer material for the reasons set forth in the aforementioned U.S. patent application Ser. No. 5,425 filed Jan. 22, 1979 in the names of A. Achari and E. T. Heiney and entitled "Improved Ceramic Element Sensor".

FIG. 9 illustrates the actual output-voltage response of a titania exhaust gas sensor exposed to exhaust gases produced by both rich and lean mixtures where these mixtures cycled between rich and lean once each second. The sensor response time is defined as the time required for the sensor to traverse from 33% to 66% of the reference voltage when the air/fuel ratio changes from lean to rich and the time required for the sensor to traverse from 66% to 33% of the reference voltage when the air/fuel ratio changes from rich to lean. The sensor response depicted in FIG. 9 is taken from an output-voltage trace of a titania sensor. The trace was obtained during a test conducted with a vapor-carburetor facility. During the test, air/fuel ratio was modulated in a step-function manner with ±1.5 air/fuel ratio variation about the stoichiometric value. Response time is fast, on the order of 10 to 20 milliseconds, and these very low values are difficult to measure.

In fabricating partial pressure of oxygen responsive element 46, a substantially pure, preferably titania, powder is prepared. As titania has two phases, the anatase phase and the rutile phase, and the rutile phase is the high temperature stable phase, the titania powder should be comprised of a substantial majority of rutile phase material. In order to convert the anatase phase material to rutile phase material, the titania material may be calcined, for example for two hours at 1150° C., and then balled milled to produce powder having small particle sizes with the majority of the powder being rutile phase material. Calcining also improves the purity of the powder by volatilizing any volatilizable impurities. The powder should have 100% of the particles smaller in size than 20 microns and should have a substantial majority of the powder with a particle size smaller than about 10 microns. The processed powders may then be ball milled with an organic binder solution to form a slurry. The slurry may thereafter be cast, formed onto a tape or sheet of material such as cellulose acetate or polytetrafluoroethylene (PTFE) after which the slurry may be air dried, to form a sheet or tape of material. Suitably sized and shaped sensor element wafers of the air dried material may then be cut from the tape for further processing. A pair of lead wires may be inserted into the sensor element and the sensor element may thereafter be sintered to a pyrometric cone equivalent number 9.

Such processing will produce a titania partial pressure of oxygen responsive ceramic element having a degree of porosity consonant with rapid transport of gases throughout the element for intimate contact with individual grains of the ceramic material. After the sensor elements have been so matured, the matured ceramic elements may then be impregnated with a solution including a substance for forming a charge transfer material. The presently preferred charge transfer material is a metallic alloy of 90% by weight platinum and 10% by weight rhodium.

A solution of platinum and rhodium in 2½% concentration may be used to apply the paltinum/rhodium charge transfer material to a porous titania sensor element 46. Solution containing nine parts by weight platinum to one part by weight rhodium (a 90/10 platinum-rhodium composition) is believed to be very satisfactory in achieving the results described herein. A solution containing platinum in the above ratio and in the amount of 2½% by weight is formed by mixture of chloroplatinic acid and rhodium chloride. The platinum and rhodium ions in the solution are intimately mixed on an atomic scale. A titania sensor element 46 sintered (fired) as previously described is immersed in the solution. The solution then is allowed to evaporate leaving crystals of platinum chloride and rhodium chloride on the sensor element. It is believed that these crystals are very fine and are so intimately mixed that, upon heating of the titania sensor element to about 900° C., the salts decompose to leave platinum and rhodium atoms mixed with one another on an atomic scale. Thus, it is believed that a true alloy of platinum and rhodium is formed by use of the above procedure. This platinum/rhodium alloy forms the charge transfer material for titania that produces the reduced low-temperature response times hereinafter described.

In the application of the solution containing the preferred charge transfer material to the metal oxide ceramic element 46, the solution having the ceramic element or elements in it preferably is placed in an environment evacuated to a vacuum level of about 711 mm Hg. The evacuated environment facilitates the removal of entrapped air from the porous metal oxide ceramic element 46. As a result, the solution is allowed to flow throughout the ceramic element 46 so that substantially all interior and exterior surfaces of the metal oxide ceramic grains are exposed to the solution. The impregnated element then is dried preferably with hot-air at about 350° C. Following this, the element 46 is heated to approximately 900° C. as was mentioned in the preceding paragraph. This continues for about one hour and decomposes the salts or compounds from which the preferred platinum/rhodium alloy charge transfer material is produced. Of course, other known techniques for applying finely-divided metal particles to substrates may be used to the extent these prove feasible for the intended sensor ceramic material and its end use. For example, if platinum is to be the charge transfer material, a solution of perhaps 2% or 5% concentration chloroplatinic acid and formaldehyde in 1:1 or equal part by weight ratio may be applied to the metal oxide ceramic element. With this solution, the step of heating in air may be accomplished at a lower temperature of about 760° C. for a longer period of time of approximately four hours. It will be appreciated that various solutions of salts or compounds for forming charge transfer materials may be used and that these solutions, or different strengths of these solutions, will result in deposits of salts which will decompose at different time-temperature combinations. Decomposition reactions at higher temperatures and/or for other periods of time may improve the bond between the ceramic grains and the charge transfer material.

In order to be assured that the charge transfer material appears as finely divided particles and is substantially uniformly distributed on the surface of the ceramic grains throughout the sensor ceramic, the charge transfer material is preferably applied as a liquid solution. This provides for the desired finely divided particles and the substantially uniform distribution, and it also increases the probability of penetration throughout the sensor ceramic. The matured sensor ceramic material should be immersed in the liquid solution for a period of time sufficient to allow the solution to flow throughout the sensor ceramic material. If the charge transfer material is not readily formed into liquid solution, an acid comprised of, inter alia, a substance capable of forming the charge transfer material may be used. In order to readily disassociate the acid to generate salts of the charge transfer material, a reducing agent such as formaldehyde or hydrazine is used in combination with the acid. In the event that use of a reducing agent, such as formaldehyde or hydrazine, is undesirable, a chloroplatanate acid solution may be used. In such an instance, the ceramic, when air dried after removal from the solution, will have deposited on the grain surfaces salts of platinum chloride. In order to remove the chloride from the deposited salts further processing would be required. This further processing could include substitution of another chemical element for the chloride component of the salt, removal of the chloride and removal of the substitute component.

Scanning photomicrographs have revealed that the solution impregnation process has been successful to a high degree in providing platinum, or other charge transfer material, distribution substantially uniformly throughout the porous titania ceramic.

Tables 1 and 2 contain data obtained in a natural gas burner having exhaust gas sensors of the design illustrated in FIGS. 1 through 3 installed in the burner's exhaust passage. The titania ceramic elements of the tested sensors were mounted in the manner illustrated in these FIGS. 1 to 3 and were electrically connected in circuit as illustrated in FIG. 4. The sensor response times were measured in accordance with the definitions of lean-to-rich (L-to-R and rich-to lean (R-to-L) response time previously given in connection with the discussion related to FIG. 9. The thermistor elements 48 in each of the tested samples were of a titania composition of substantially greater density than that of the titania oxygen sensing element 46, which was fabricated as prescribed herein and, therefore, quite porous. Of course, no charge transfer material was applied to the thermistor elements 48 because they are intended to have very limited response to variations in the partial pressure of oxygen in the gaseous medium to which they are exposed. Also, both the oxygen sensing elements 46 and the thermistor elements 48 of the sample exhaust gas sensors were made from the same respective batches of titania and were fired or sintered in the same manner according to their respective applications as oxygen sensing elements and thermistors.

TABLE 1

ELAPSED TIME UNTIL RESPONSE

| Sensor Sample Number | Elapsed time (Minutes:Seconds) until First Excursion of Sensor Output Voltage from 33% to 66% of Applied Voltage | | | | | |
|---|---|---|---|---|---|---|
| | $T_1$ | $T_2$ | $T_3$ | $T_4$ | $T_5$ | $T_6$ |
| N1 | — | — | — | 1:20 | :55 | :23 |
| N2 | — | — | — | 1:45 | :43 | :23 |
| N3 | — | — | 5:25 | 1:15 | :55 | :27 |
| N4 | — | — | — | 2:10 | 1:10 | No data |
| P1 | — | 3:45 | 1:45 | :43 | :25 | :17 |
| P2 | — | 4:20 | 1:45 | :38 | :20 | :17 |
| P3 | — | 5:30 | 1:40 | :50 | :25 | :15 |
| C1 | 10:00 | 3:40 | 1:30 | :31 | :22 | :10 |
| C2 | 9:15 | 3:15 | 1:35 | :40 | :20 | :10 |
| C3 | — | 3:40 | 1:40 | :33 | :22 | :12 |
| C4 | — | 3:25 | 1:30 | :33 | :20 | :09 |
| E1 | 2:15 | 1:05 | :45 | :17 | :10 | Approx.:02 |
| E2 | 2:50 | 1:05 | :30 | :15 | :07 | Approx.:02 |
| E3 | 2:35 | 1:15 | :40 | :40 | :10 | Approx.:02 |
| $E_{avg.}$ | 2:33 | 1:08 | :38 | :17 | :09 | :02 |

Table 2

TITANIA SENSOR RESPONSE TIME

| Sensor SAMPLE Number | Lean-to-Rich Response Time (ms) | | | | | | Rich-to-Lean Response Time (ms) | | | | | | Lean-to-Rich Response Time (ms) | | | | | |
|---|---|---|---|---|---|---|---|---|---|---|---|---|---|---|---|---|---|---|
| | $T_1$ | $T_2$ | $T_3$ | $T_4$ | $T_5$ | $T_6$ | $T_1$ | $T_2$ | $T_3$ | $T_4$ | $T_5$ | $T_6$ | $T_1$ | $T_2$ | $T_3$ | $T_4$ | $T_5$ | $T_6$ |
| N1 | — | — | — | 404 | 18 | 12 | — | — | — | 234 | 74 | 36 | — | — | — | 376 | 16 | 10 |
| N2 | — | — | — | 666 | 30 | 14 | — | — | — | 230 | 56 | 28 | — | — | — | — | 30 | 14 |
| N3 | — | — | 5260 | 172 | 34 | 22 | — | — | 1040 | 304 | 34 | 24 | — | — | 4980 | 162 | 38 | 22 |
| N4 | — | — | — | 466 | 66 | * | — | — | — | 148 | 44 | * | — | — | — | 506 | 66 | * |
| P1 | — | 1980 | 216 | 18 | 16 | 16 | — | 490 | 388 | 152 | 40 | 26 | — | 1896 | 182 | 16 | 18 | 18 |
| P2 | — | 1200 | 212 | 34 | 14 | 12 | — | 360 | 260 | 90 | 28 | 16 | — | 1136 | 218 | 18 | 12 | 12 |
| P3 | — | 2070 | 178 | 22 | 20 | 16 | — | 490 | 388 | 154 | 40 | 32 | — | 2090 | 206 | 18 | 20 | 22 |
| C1 | 3280 | 310 | 52 | 12 | 4 | 4 | 460 | 180 | 148 | 92 | 30 | 14 | 3760 | 356 | 52 | 8 | 6 | 4 |
| C2 | 3800 | 304 | 56 | 28 | 8 | 4 | 600 | 164 | 240 | 140 | 10 | 12 | 3240 | 322 | 52 | 32 | 20 | 6 |
| C3 | — | 336 | 52 | 22 | 6 | 4 | — | 120 | 146 | 94 | 20 | 14 | — | 312 | 48 | 20 | 4 | 6 |
| C4 | — | 692 | 78 | 18 | 6 | 6 | — | 84 | 210 | 120 | 34 | 14 | — | 712 | 74 | 22 | 8 | 6 |
| E1 | 124 | 94 | 18 | 6 | 6 | 4 | 90 | 38 | 26 | 26 | 4 | 10 | 132 | 78 | 22 | 4 | 6 | 6 |
| E2 | 70 | 36 | 8 | 8 | 16 | 14 | 68 | 14 | 8 | 12 | 10 | 6 | 64 | 36 | 8 | 8 | 18 | 14 |
| E3 | 172 | 64 | 16 | 28 | 10 | 6 | 110 | 52 | 34 | 4 | 8 | 14 | 158 | 92 | 16 | 26 | 10 | 8 |
| $E_{avg.}$ | 122 | 65 | 14 | 14 | 11 | 8 | 80 | 35 | 23 | 14 | 7 | 10 | 118 | 69 | 15 | 13 | 11 | 9 |

$T_1$ = Sensor Tip at 286° C., Gas at 426°–428° C.
$T_2$ = Sensor Tip at 347°–350°C., Gas at 484°–489° C.,
$T_3$ = Sensor Tip at 412°–414° C., Gas at 537°–539° C.
$T_4$ = Sensor Tip at 511°–524° C., Gas at 619°–627° C.
$T_5$ = Sensor Tip at 660°–668° C., Gas at 692°–697° C.
$T_6$ = Sensor Tip at 749°–771° C., Gas at 786°–798° C.
* = No Data
NOTE: At temperatures $T_4$, $T_5$, and $T_6$ air/fuel ratio was cycled at a rate of four seconds lean, four seconds rich, etc.

Sensor samples N1, N2, N3 and N4 exhaust gas oxygen sensors each had a porous titania oxygen sensing element 46 to which no charge transfer material was applied, i.e., these sensor samples were simply metal oxide ceramic sensors connected with a thermistor of identical material in an electrical circuit as shown in FIG. 4, except that their response characteristics were obtained by measurement with a Brush recorder connected in parallel with the two megohm impedance shown in FIG. 4 as representing the input impedance of an electronic feedback fuel control system.

Sensor samples P1, P2 and P3 were identical to the samples N1 to N4 except for the application to each of the former samples of a platinum paste. The platinum paste was applied with a brush to the exterior surfaces of the oxygen sensing element 46 in each of sensors P1, P2 and P3 and, after application, was dried rapidly with hot-air at a temperature of about 350° C. The platinum paste as applied to the porous ceramic elements was dispersed in an amyl acetate solvent and the mixture had a viscosity similar to that of shellac. After application of the platinum paste and hot-air drying thereof, the oxygen sensing ceramic elements were fired at about 900° C. for one hour.

Sensor samples E1, E2 and E3 were made in accordance with the preferred form of the invention as described herein and in related patent application Ser. No. 5,425 to Achari et al, as was previously referenced. These samples E1 to E3 had a 90% Pt/10% Rh charge transfer material applied to them by immersion in a solution in an evacuated environment in accordance with the preferred procedure previously described. Sensor samples C1, C2, C3 and C4 were identically processed, except that the Pt/Rh solution was applied by immersion in an environment of air at normal atmospheric pressure. Also, instead of hot-air drying of the solution at about 350° C., the oxygen sensing elements 46 of sensor samples C1 to C4 were air dried at room temperature and then heated to 900° C. to decompose the platinum and rhodium salts or compounds in accordance with the preferred procedure used with the corresponding oxygen sensing elements 46 of sensor samples E1, E2 and E3. The sensor sample designation $E_{avg}$ in Tables 1 and 2 is not real sample, but rather is used to indicate the average of the test results obtained for the three sensors E1, E2 and E3. Thus, the $E_{avg}$ test results are calculated numbers.

All of the sensor samples were tested in the natural gas burner at six different exhaust gas temperatures indicated as $T_1$, $T_2$, $T_3$, $T_4$, $T_5$ and $T_6$. Corresponding sensor tip temperatures were measured with a thermocouple positioned adjacent and between the ceramic elements 46 and 48 of each of the sensor samples. The actual sensor tip and exhaust gas temperatures corresponding to the designations $T_1$ through $T_6$ are shown at the bottom of Table 2. In the process used to obtain the data in the tables, the sample test sequence was varied deliberately and standard oxygen sensing devices were used to aid in verifying the test results. The mixture of natural gas and air supplied to the burner was varied cyclically with an air/fuel mixture which was lean of stoichiometry for six seconds, rich for the next six seconds, lean again for six seconds, etc. Response times for the sensor samples are in milliseconds.

For acceptability for use in engine closed-loop fuel control systems for motor vehicles, a titania sensor should have a response time of 300 ms or less at a sensor tip temperature of 350° C. and should have a response time of 100 ms or less at a sensor tip temperature of 850° C. Also, for use in motor vehicle systems, an oxygen sensor must develop its initial response soon after a cold engine is started so that closed-loop control can begin at the earliest possible time. This aids in minimizing undesirable exhaust emissions in three-way catalyst exhaust emission control systems.

Table 1 provides data, in minutes and seconds, of the time elapsed between insertion of each of the exhaust gas sensor samples in the exhaust conduit of the natural gas burner and the instant of occurrence of the first excursion of the sensor output voltage across the response boundary between 33% and 66% of voltage applied to the sensor. In other words, this is the time elapsed between subjecting the sensor to exhaust gases and initial detection by the sensor of an excursion of the air/fuel mixture across stoichiometry. The time measurements began when each sensor, initially at room temperature, had been screwed finger-tight into the exhaust conduit of the natural gas burner.

The data in Table 1 clearly establishes the significance of the charge transfer material with respect to capability of the sensors to sense air/fuel ratio excursions about stoichiometry at low exhaust gas and sensor tip temperatures. Sensor samples E1, E2 and E3 exhibit outstanding performance, whereas the sensor samples N1 to N4 had no responses at all at the lower temperatures. Intermediate results were achieved with the other sensors.

In Table 2, response times for the various sensor samples are given for each of the six temperatures $T_1$ through $T_6$ and for three consecutive air/fuel ratio excursions at each of the temperatures. Again, the superior response times of the sensor samples having charge transfer material on their oxygen sensing elements are demonstrated. Sensor samples E1, E2 and E3 clearly have the lowest and best response times and are the sensors believed to have the most uniformity of dispersion of charge transfer material throughout the volume of the oxygen sensing elements. Sensor samples C1, C2, C3 and C4 are second best and this is thought to be due to less penetration of the Pt/Rh solution into the oxygen sensing element volume because an evacuated environment was not used, nor was the hot-air drying of the solution.

Sensor samples P1, P2 and P3 were third best in response characteristics and appear to be unsatisfactory for use in most engine fuel-control applications. The charge transfer material, applied by brushing a solution on the oxygen sensing elements of these sensors, probably did not provide a sufficiently dispersed charge transfer material on all of the interior surfaces of the porous elements. Thus, it is expected that the transfer of oxygen into and out of the titania crystal structure at low temperatures was not greatly facilitated by use of the charge transfer material.

Sensor samples N1 to N4, having no charge transfer material, did not exhibit satisfactory response times until sensor tip temperatures in excess of 600° C. were reached. This again points out the significance of the charge transfer material.

Table 3 provides data that demonstrates that the spacing of the electrodes 40 and 44 in the oxygen sensing elements 46, and 42 and 44 in the thermistor element 48, is not critical to exhaust gas sensor operation. Table 3 lists the spacing between platinum electrode wires embedded in titania oxygen sensing and thermistor elements 46 and 48. The spacing is expressed in millimeters. Both low and high electrode spacings were used and these differed from one another by a factor of about three. All possible combinations of low and high electrode spacing for the oxygen sensing and thermistor elements were used (a total of four combinations). Response times at exhaust gas temperatures of 499° C. and 727° C. were satisfactory for both rich-to-lean and lean-to-rich air/fuel ratio excursions.

The data for Table 3 was obtained with titania oxygen sensing elements that had been immersed in solutions containing platinum in an amount of 1% by weight. The electrode spacings were measured on X-rays taken of the chips with a microscope having a forty-times-size magnification and a calibrated ocular. Two samples of each sensor were fabricated and their response times were averaged. The air/fuel ratio of the mixture supplied to the natural gas burner on which the tests were conducted had a rich-to-lean and lean-to-rich cycling rate of 0.125 H$_Z$.

TABLE 3

EXHAUST GAS SENSOR RESPONSE TIME vs. ELECTRODE SPACING

| Spacing of Electrode Wires 40 and 44 in Oxygen Sensing Element 46 (mm) | Spacing of Electrode Wires 42 and 44 in Thermistor Element 48 (mm) | At 499° C. Gas Temp R-to-L | At 499° C. Gas Temp L-to-R | At 727° C. Gas Temp R-to-L | At 727° C. Gas Temp L-to-R |
|---|---|---|---|---|---|
| 6.274 (low) | 18.389 (high) | 62 | 79 | 25 | 8 |
| 18.593 (high) | 6.629 (low) | 48 | 147 | 22 | 22 |
| 6.248 (low) | 7.315 (low) | 53 | 121 | 26 | 6 |
| 17.062 (high) | 18.567 (high) | 78 | 94 | 19 | 6 |
|  | Average Response Time | 60 | 110 | 23 | 10 |

Based upon the foregoing description, what is claimed is:

1. An improved sensor of the type having a metal oxide ceramic element that undergoes changes in resistivity in response to variations in the partial pressure of oxygen in the gaseous medium to which the metal oxide ceramic element is exposed, the metal oxide ceramic element having electrodes in spaced apart relationship, the electrodes extending from the metal oxide ceramic element to permit the resistance between them to be sensed, and the metal oxide ceramic element being adapted to be immersed in the gaseous medium, wherein the improvement comprises:

the metal oxide ceramic element is titania (TiO$_2$) and is porous to enlarge, as compared to a less porous material, the amount of titania element surface area exposed to the gaseous medium, and the titania element surface area has on it, and substantially throughout the volume of the titania ceramic element, a discontinuous charge transfer material comprising a metal having free electrons, whereby, the response time of the titania ceramic element is substantially reduced due to the presence of the charge transfer material, in the lower portion of the temperature range over which the titania ceramic element responds to variations in the partial pressure of oxygen in the gaseous medium;

the sensor includes a second ceramic element less responsive to variations in the partial pressure of oxygen in the gaseous medium that is the first-mentioned ceramic element, and includes means for electrically connecting the first-mentioned ceramic element and second ceramic element in circuit such that output voltage changes from 33% to 66%, and vice versa, of applied voltage occur in less than about 300 milliseconds when the ceramic elements are at a temperature of about 350° C.

2. An improved sensor according to claim 1 wherein the titania ceramic element is made from titania particles a substantial majority of which are of the rutile phase, 100% of the titania particles are smaller in size than 20 microns and a substantial majority thereof are smaller in size than 10 microns, and platinum is dispersed throughout the titania in the form of platinum particles deposited on the particles of titania, the platinum particles being in majority located in proximity to intergranular boundaries of the titania, the platinum particles being substantially smaller in size than the titania particles and being deposited thereon by: (a) immersion of the titania in a solution containing a platinum compound, the immersion taking place in an evacuated environment allowing entrapped air to be removed from the titania and allowing the solution to flow through the porous titania; (b) air drying the previously immersed titania; and (c) heating the air-dried titania in air for a time period and at a temperature sufficient to reduce the deposited platinum compound remaining after air drying of the solution to platinum particles and to sinter the platinum particles to the titania particles.

3. An improved sensor according to claim 1, wherein the titania ceramic element of the sensor has had the charge transfer material applied to the titania ceramic element by immersion of the titania ceramic element in a solution containing ions of the metal, the solution upon drying having formed deposits of a salt or compound, the salt or compound deposits having been decomposed to form the discontinuous metal charge transfer material.

4. An improved sensor according to claim 3, wherein the titania ceramic element, after its immersion in the solution, has been hot-air dried.

5. An improved sensor according to claims 3 or 4, wherein the titania ceramic element of the sensor has had the solution with the immersed titania ceramic element placed in an evacuated environment, thereby, to facilitate the removal of air from the porous titania ceramic element and to promote, thereby, dispersion of the solution throughout the porous titania ceramic element.

* * * * *